United States Patent
Goetz et al.

(10) Patent No.: US 9,996,669 B2
(45) Date of Patent: Jun. 12, 2018

(54) INTELLIGENT DISCOVERY OF MEDICAL DEVICES BY A PROGRAMMING SYSTEM

(75) Inventors: Steven M. Goetz, North Oaks, MN (US); Touby A. Drew, Golden Valley, MN (US); Earle T. Roberts, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 2143 days.

(21) Appl. No.: 11/800,423

(22) Filed: May 4, 2007

(65) Prior Publication Data

US 2008/0140160 A1    Jun. 12, 2008

Related U.S. Application Data

(60) Provisional application No. 60/873,147, filed on Dec. 6, 2006.

(51) Int. Cl.
*A61N 1/00* (2006.01)
*G06F 19/00* (2018.01)
*A61N 1/372* (2006.01)

(52) U.S. Cl.
CPC ..... *G06F 19/3418* (2013.01); *A61N 1/37288* (2013.01); *G16H 40/20* (2018.01); *G16H 40/40* (2018.01)

(58) Field of Classification Search
USPC ....................................... 607/2, 60; 128/903
See application file for complete search history.

(56) References Cited

U.S. PATENT DOCUMENTS

| | | | |
|---|---|---|---|
| 6,141,588 A * | 10/2000 | Cox et al. | ........................... 607/9 |
| 6,250,309 B1 | 6/2001 | Krichen et al. | |
| 6,418,346 B1 | 7/2002 | Nelson et al. | |
| 6,442,433 B1 | 8/2002 | Linberg | |
| 6,480,745 B2 | 11/2002 | Nelson et al. | |
| 6,482,154 B1 | 11/2002 | Haubrich et al. | |
| 6,516,227 B1 | 2/2003 | Meadows et al. | |
| 6,574,511 B2 | 6/2003 | Lee | |

(Continued)

FOREIGN PATENT DOCUMENTS

WO    WO 03/095024 A2    11/2003

OTHER PUBLICATIONS

Reply to Written Opinion for corresponding patent application No. PCT/US2007/010962. filed Aug. 11, 2008, 4 pages.
Notification of Transmittal of the International Search Report and the Written Opinion of the International Searching Authority, or the Declaration for corresponding patent application No. PCT/ US2007/ 010962, dated Feb. 6, 2008, 12 pages.
Notification of Transmittal of the International Preliminary Report on Patentability for corresponding patent application No. PCT/ US2007/010962, dated Nov. 10, 2008, 10 pages.
Commuication pursuant to Article 94(3) EPC for corresponding European Patent Application No. 07 776 812.5-1952, dated Oct. 7, 2013, 3 pages.

(Continued)

*Primary Examiner* — Erica Lee
(74) *Attorney, Agent, or Firm* — Shumaker & Sieffert, P.A.

(57) ABSTRACT

Techniques for automatically identifying medical devices, e.g., implantable medical device, using wireless communications in order to communicate with the medical devices are described. For instance, a programming system securely discovers a set of medical devices which have the capacity to communicate using wireless communication links. The programming system may then apply one or more search heuristics to identify a set of discovered medical devices that are likely to be a medical device with which a user desires to interact. When the user selects the desired one of the identified medical devices, the programming system launches a device interaction application associated with the desired medical device. The user may use the device interaction application to interact with the desired medical device.

22 Claims, 5 Drawing Sheets

(56) References Cited

U.S. PATENT DOCUMENTS

| | | |
|---|---|---|
| 6,599,250 B2 | 7/2003 | Webb et al. |
| 6,665,565 B1 | 12/2003 | Stomberg et al. |
| 6,978,181 B1 | 12/2005 | Snell |
| 2002/0123673 A1* | 9/2002 | Webb et al. .................. 600/300 |
| 2003/0212311 A1* | 11/2003 | Nova et al. ................... 600/300 |
| 2003/0220673 A1* | 11/2003 | Snell .............................. 607/60 |
| 2004/0073276 A1* | 4/2004 | Samuelsson ................... 607/60 |
| 2004/0167587 A1 | 8/2004 | Thompson |
| 2005/0015115 A1* | 1/2005 | Sullivan et al. .................. 607/5 |
| 2005/0113885 A1* | 5/2005 | Haubrich et al. .............. 607/60 |
| 2006/0020304 A1* | 1/2006 | Torgerson et al. ............. 607/60 |
| 2006/0064020 A1* | 3/2006 | Burnes et al. ................ 600/481 |
| 2006/0089684 A1 | 4/2006 | Blaha et al. |
| 2006/0241701 A1 | 10/2006 | Markowitz et al. |

OTHER PUBLICATIONS

Response to European Examination Report dated Oct. 6, 2016, from counterpart European Application No. 7776812.5, filed on Feb. 15, 2017, 9 pages.

Communication pursuant to Article 94(3) EPC, from counterpart European Application No. 07776812.5, dated Oct. 6, 2016, 6 pp.

\* cited by examiner

INTELLIGENT DISCOVERY OF MEDICAL DEVICES BY A PROGRAMMING SYSTEM

This application claims the benefit of provisional application No. 60/873,147, filed Dec. 6, 2006, the entire content of which is incorporated herein by reference.

TECHNICAL FIELD

The invention relates to medical devices, and particularly, to medical device communication.

BACKGROUND

A clinician may implant a medical device within a person or animal (i.e., a patient). The medical device may provide therapy to the patient. For example, the medical device may deliver electrical stimulation to neural or other tissues of the patient to alleviate a symptom, such as pain. In some cases, the clinician may need to program or reprogram the implanted medical device while the medical device is implanted in the patient. For example, the clinician may need to adjust an amplitude, pulse width, or pulse rate of the stimulation, or change the configuration of implanted electrodes through which the stimulation is delivered.

The implanted medical device may be equipped with one or more wireless communications technologies to enable the clinician to program the implanted medical device while the medical device remains implanted in the patient. For example, the clinician may hold an antenna for an external programming device (or the device itself) equipped with an equivalent wireless communication technology close to the patient. The clinician may then use the external programming device to wirelessly communicate with the implanted medical device. These wireless communications may, for example, reprogram the implanted medical device or retrieve data from the medical device.

SUMMARY

In general, the invention is directed to techniques for automatically identifying medical devices using wireless communications in order to communicate with the medical devices. For instance, a programming system securely discovers a set of medical devices, e.g., implanted medical devices, that have the capacity to communicate using wireless communication links. The programming system may then apply one or more search heuristics to identify a subset of the discovered medical devices which are likely to be an implantable medical device with which a user desires to interact. When the user selects the desired one of the identified medical devices, the programming system may launch one or more device interaction applications associated with the desired medical device. The user may use the software applications to interact with the desired medical device.

In one embodiment, a method comprises discovering a set of medical devices using one or more communication links. In addition, the method comprises applying one or more search heuristics to the set of discovered medical devices to identify one or more medical devices in the set that are likely to be a medical device with which a user desires to interact. The method also comprises launching one or more device interaction applications associated with the desired medical device for use in programming the desired medical device.

In another embodiment, the invention is directed to a programming system that comprises a discovery service module that discovers a set of medical devices with which a programming system communicates using one or more communication links, and a set of one or more device discovery managers that apply one or more search heuristics to the set of discovered medical devices to identify one or more medical devices in the set that are likely to be a medical device with which a user desires to interact; and launches one or more device interaction applications associated with the desired medical device for use in interacting with the desired medical device.

In another embodiment, a computer-readable medium comprises instructions. The instructions cause a programmable processor to discover a set of medical devices with which a programming system communicates using one or more communication links. The instructions also cause the processor to apply one or more search heuristics to the set of discovered medical devices to identify one or more medical devices in the set that are likely to be a medical device with which a user desires to interact. In addition, the instructions cause the processor to launch one or more device interaction applications associated with the desired medical device, for use by a user to interact with the desired medical device.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
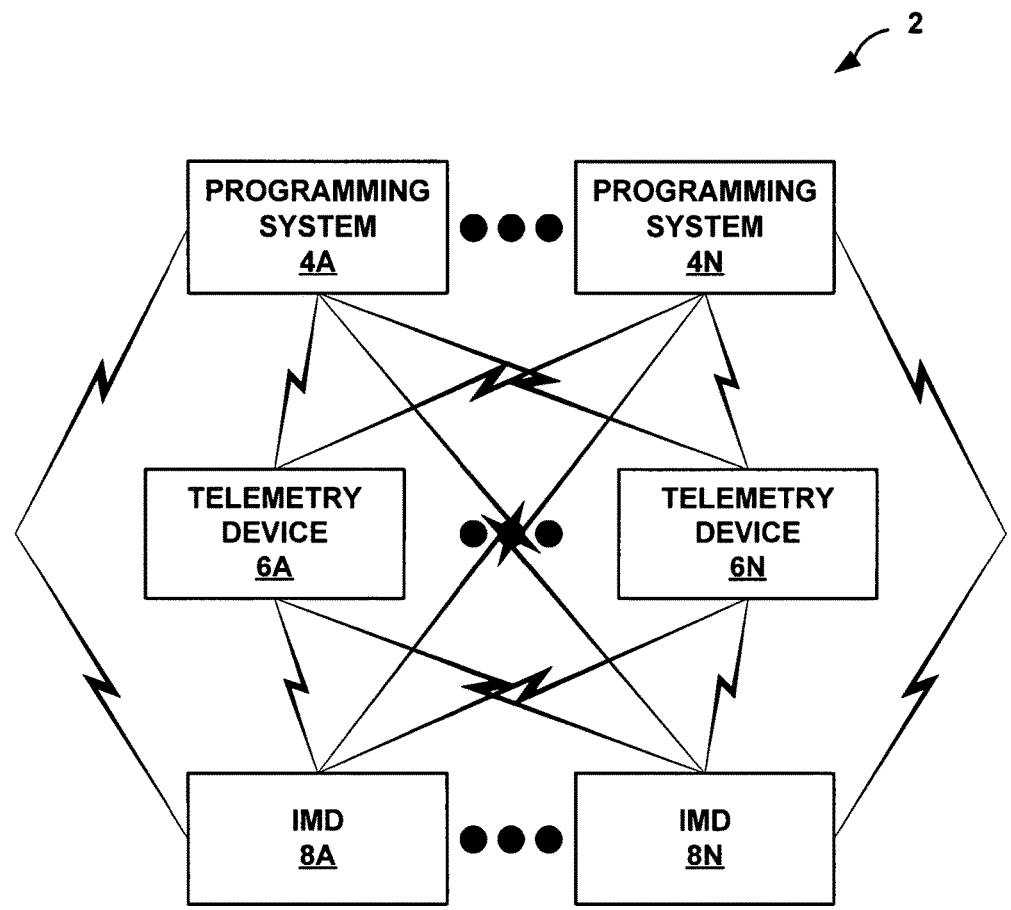
FIG. 1 is a block diagram illustrating an example environment in which programming systems identify medical devices.

FIG. 1 is a block diagram illustrating an example environment 2 in which programming systems 4A through 4N identify implantable medical devices (IMDs) 8A through 8N, As illustrated in the example of FIG. 1, programming systems 4A through 4N (collectively, "programming systems 4") may communicate through wireless links to telemetry devices 6A through 6N (collectively, "telemetry devices 6"). Telemetry devices 6 may communicate through wireless links to IMDs 8A through 8N (collectively, "IMDs 8") and programming systems 4. In addition, programming systems 4 may communicate through wireless links directly with IMDs 8. Programming systems 4, telemetry devices 6, and IMDs 8 may use wireless communication methods that include, but are not limited to, acoustic, radio frequency, and inductive links. Although not illustrated in the example of FIG. 1, one or more of programming systems 4 and telemetry devices 6 may communicate using wired physical communication links.

Programming systems 4 may be computing devices that execute device interaction software applications. For example, programming systems 4 may be personal computers, laptop computers, handheld computers, network servers, mainframe computers, proprietary hardware systems, and so on. A device interaction software application may be a specialized software application that is designed to provide user interaction with medical devices. A device interaction software application may display an interface through which a clinician may enter new program instructions for a medical device, configure settings of the medical device, view configurations of a medical device, retrieve information from a medical device, and so on. In addition, a device interaction software application may display information received from a medical device. For example, a device interaction software application may display settings currently used by the medical device, remaining battery life, usage statistics, etc. Programming systems 4 may be, for example, clinician programming devices that take the form of dedicated clinician programming hardware, or general purpose computing devices that execute software providing clinician programming functionality.

Telemetry devices 6 may be handheld devices used to communicate with IMDs 8. For example, a clinician may carry one of telemetry devices 6 into an examination room in order to communicate with one of IMDs 8 implanted in a patient in the examination room. Telemetry devices 6 may be specialized devices, laptop computers, personal digital assistants, cellular telephones, or any device capable of communicating with a medical device, e.g., any device capable of telemetric communication with an IMD. In some embodiments, telemetry devices 6 may be physically attached to programming systems 4.

In some embodiments, telemetry devices 6 may be patient programmer devices. A patient programmer device is an external device, which may be specially pre-configured to program an implantable medical device. A patient may be able to use a personal, dedicated patient programmer device without the assistance of a clinician. For example, a patient may use a patient programmer device to control therapy, to perform diagnostics, or as a personal convenience-based system functionality that may include, but is not limited to, recharging of the battery of the patient's implanted medical device.

In other embodiments, one or more of telemetry devices 6 may take the form of an external patient monitor. Patient monitors may monitor one or more physiological characteristics of a patient. For example, a patient monitor may alert a patient when blood pressure rises above a certain threshold, or may provide loop recording capabilities for one or more physiological characteristics.

Some patient programmer devices may be configured to communicate only with a particular one of IMDs 8. Furthermore, this IMD may be configured to communicate only with a particular patient programmer device. As used herein, such devices may be said to be "bonded." For example, a patient programmer device and an IMD may share an encryption key known only to the patient programmer device, and the IMD is only able to communicate using this encryption key. Such bonding may help prevent another device from accidentally or maliciously communicating with an IMD, Furthermore, some patient programmer devices may hold security information required to communicate securely with an IMD. In another example, a patient programmer device may include an activator that may be used to enable a secure session with an IMD, either as the primary method of establishing a secure session with the IMD or as a secondary method of establishing a secure session with the IMD.

Telemetry devices 6 may communicate with programming systems 4 over wired or wireless communication links. For example, programming system 4B (not shown) may communicate with telemetry device 6A via a local wireless communication link, which may be, for example, a radio-frequency or infra-red link. The communication may be according to any of a variety of standards, such as the Bluetooth, 802.11, or Infrared Data Association (IrDA) communication standards. As another example, programming system 4A may communicate with telemetry device 6B (not shown) using a Universal Serial Bus (USB) cable, an Ethernet cable, or otherwise. Furthermore, programming systems 4 may communicate with telemetry devices 6 over a local or wide-area network, such as the Internet.

IMDs 8 may be any of a wide variety of implantable medical devices that have the capacity to communicate using wireless links. For example, IMDs 8 may be heart pacemakers, cochlear implants, heart defibrillators, drug delivery modules, electronic prosthetic devices, neurostimulators, and so on. One or more of IMDs 8 may be implanted in a single patient. However, system 2 does not require IMDs 8 to be actually implanted in one or more patients. For example, a clinician may wish to use system 2 to interact with one or more of IMDs 8 prior to implanting IMDs 8 into a patient. Furthermore, the techniques described in this disclosure are not limited to embodiments in which the discoverable medical devices are implantable. In other embodiments, any type of medical device may be discovered using the techniques of the invention. For instance, these techniques may be applicable to the discovery and identification of telemetry devices 6 by programming systems 4.

In general, programming systems 4 may require the capacity to communicate with more than one type of medical device. For example, programming systems 4 may require the capacity to communicate with a neurostimulator manufactured by a first vendor and the capacity to communicate with a neurostimulator manufactured by a second vendor. As another example, programming systems 4 may require the capacity to communicate with different devices manufactured by a single vendor, or different versions or generations of a single type of medical device.

Each type of IMD may or may not share a common communication method. For example, IMD 8A may communicate using more recent, far-field proprietary RF communication protocol, and IMD 8B may communicate using an older, near-field proprietary communication protocol. In addition, each type of IMD may or may not require that programming systems 4 use a different type of device interaction software application for programming the IMD.

In order to make it easier for a clinician to use the correct device interaction software application of one of IMDs 8, programming systems 4 may include a method for automatically detecting what type of IMD is present and automatically launching a device interaction software application associated with that type of IMD. Automatically identifying and launching appropriate device interaction software applications may save time and reduce the need for a clinician to memorize which device interaction software application is associated with each type of IMD.

One or more of IMDs 8 may use near-field wireless communication links, e.g., near field device telemetry links. A near-field wireless communication link may only communicate information over a short distance. For example, an IMD that uses a near-field communication link might only be able to communicate with one of telemetry devices 6 when a clinician holds the telemetry device to a patient's skin over the IMD.

However, one or more of IMDs 8 may additionally or alternatively be configured to communicate using far-field wireless communication links, e.g., far field telemetry links. A far-field wireless communication link may communicate information a significantly greater distance than a near-field wireless communication link. For example, a far-field wireless communication link may facilitate communication at distances of an arm's length or greater. Further, one of IMDs 8 may use a local wireless communication link such as a Medical Implant Communication Service (MICS) band radio as a far-field wireless communication link to communicate with other devices at a range of up to 100 meters. Devices using other far-field wireless communication technologies may be able to communicate with other devices at even greater distances.

The use of far-field wireless communication links may present several advantages over the use of near-field wireless communication links. For example, a clinician or technician may use one of telemetry devices 6 to communicate with one of IMDs 8 that uses a far-field wireless communication link while remaining outside a sterile area. This may prevent the spread of bacteria, viruses, or other dangerous materials (e.g., radioactive material, toxic chemicals, etc.) to the patient and vice versa.

Because IMDs 8 using far-field wireless communication links may communicate over greater distances, several ones of IMDs 8 may be within range of a single one of telemetry devices 6 or programming systems 4. In other words, a single one of telemetry devices 6 may be within range of multiple ones of IMDs 8 (as shown in the example of FIG. 1). Moreover, a single one of programming systems 4 may be wirelessly within range of and/or coupled via wired connection to a plurality of telemetry devices 6.

Devices that relay wireless communications may increase the number of devices within range of one of programming systems 4. For example, programming system 4A might not be able to communicate directly with IMD 8A because IMD 8A is outside the range of programming system 4A. However, if telemetry device 6A is with range of programming system 4A and IMD 8A, telemetry device 6A may relay wireless communications from programming system 4A to IMD 8A. In this way, if each of programming system 4A, telemetry device 6A, and IMD 8A individually communicate over a range of 10 meters, telemetry device 6A may, by relaying communications, effectively extend the range of programming system 4A to 20 meters. Additional relays, or the use of a LAN or WAN, may extend this range even further. For this reason, one of programming systems 4 may potentially be in range of a large number IMDs 8 at multiple different locations, e.g., different buildings, cities, states, or countries.

When a clinician begins a programming session on one of programming systems 4, the programming system may poll pertinent devices for which the programming system has stored identification information in a local or remote database. In addition, the programming system may broadcast, using one or more communication links, a request for devices within range of the programming system to identify themselves. For example, the programming system may poll or broadcast a request using one or more Bluetooth links, one or more USB links, one or more Wi-Fi links, and so on. Any devices within range of the poll request or the broadcast request from the programming system may send responses to the programming system.

After receiving a response from a device, the programming system may send a request to the responding device requesting that the responding device poll or broadcast a request to see all devices within range of the responding device. In response to this request, the responding device may poll or broadcast a request and send a response containing a list of all devices within range of the responding device to the programming system. In other embodiments, responding devices may have already independently queried other devices to determine which other devices are available for communication when the request for such information is received. In such embodiments, the responding device may send such information in response to the request without further querying other devices in its communication range. Polling pertinent devices may be advantageous over broadcasting requests for devices to identify themselves because polling pertinent devices may not require a device to make its identity publicly available to all other devices. For this reason, polling pertinent devices may be more secure than broadcasting requests for devices to identify themselves.

In either case, the programming system may continue the querying process a certain number of times. In this way, the programming system may internally construct a directed graph data structure. Each edge or path in the directed graph data structure may represent a hop away from the programming system. Each node in the directed graph data structure may represent a device. The nodes at any point may be, for example, telemetry devices 6 or IMDs 8, e.g., there may be multiple telemetry device 6 hops prior to reaching an IMD 8. Because a single device may be in range of multiple other devices, a single device may be represented in the directed graph data structure multiple times. For this and other reasons, the directed graph data structure may become so extensive that it may be impractical or inconvenient for a clinician to manually select a desired device from the directed graph data structure.

Programming systems 4 may use one or more search heuristics to sort or prune the directed graph data structure such that a clinician may more easily select the desired device. As used in this disclosure, a search heuristic may be a criterion that concretely defines an order to and/or a subset of a search space. For example, a search heuristic may sort or limit the directed graph data structure based on whether or not devices possess specific characteristics or a search heuristic may be a criterion that sorts the directed graph data structure based on probabilities. In this example, one of programming systems 4 may use the search heuristics to determine a short list of devices in the directed graph data structure that are likely to be the desired device. The programming system 4 may compare the search heuristics to information received from the telemetry devices 6 and IMDs 8 in their responses to the querying/discovery process described above. Based on the comparison, a subset of the discovered telemetry devices 6 or IMDs 8 that are likely to be a medical device with which a user desires to interact may be identified, e.g., telemetry devices and IMDs that do not provide information matching the search heuristics may be pruned from the directed graph data structure.

The programming system may then display this list in a user interface. A clinician may interact with this user interface to select the desired device. If the desired device is not on the list presented by the programming system, the clinician may select a button or other input medium on the interface to display more devices. In some example embodiments, the programming system may display this list before the programming system finishes searching for devices. In these embodiments, the programming system may add devices that conform to the search heuristics to the list as the programming system identifies such devices.

After the clinician selects the desired device, the programming system may establish a secure communication link with the device. In some embodiments, the desired device is selected automatically.

Programming systems 4 may facilitate user input of, optional automatic secure storage of, and automatic secure retrieval of security information used by programming systems 4 to communicate with or utilize IMDs 8. Programming systems 4 may store this security information locally or on an external device. One of programming systems 4 may access the security information either prior to or during device discovery from either external storage devices, one of IMDs 8, or by synchronizing information with other external programming equipment with which the programming system has been able to communicate with presently or in the past. For example, programming systems 4 may access the security information for an IMD 8 implanted in a patient by accessing a patient programming device, i.e., telemetry device 6, that is dedicated to holding the security information for the IMDs 8 implanted in the patient.

All or part of the information that serves as input or is stored for reference by programming systems 4 may be stored securely as appropriate to comply with privacy mandates or regulations, such as the mandates of the Health Insurance Portability and Accountability Act of 1996 (HIPPA). These mandates include data privacy, prevention of and recovery from data corruption, prevention of and recovery from data misuse through malicious intent, and other mandates. This secure storage may include, but is not limited to, encrypting the data using a cipher (e.g., Advanced Encryption Standard ("AES")), and/or incorporating access control limitations (e.g., passwords). The secure storage may be a database that protects and offers fast access to the required security information (e.g., through index searches). At the option of an administrator of system 2, the database may be secured or unsecured.

The techniques described in this disclosure may also be applicable to the identification of telemetry devices 6 (including patient programmer devices and telemetry heads). For example, IMDs 8 in FIG. 1 could be replaced with one or more additional levels of telemetry devices. Applying these techniques to the identification of telemetry devices may be useful when attempting to identify telemetry devices to reprogram. For example, telemetry device 6A may be a patient programmer device that is bonded to an IMD implanted in a patient. The patient may use this patient programmer device to cause the implanted IMD to release additional medicine, or begin or adjust a stimulation therapy.

In this example, it may be useful to identify this telemetry device in order to launch one or more device interaction applications associated with this telemetry device. A clinician may then use these device interaction applications to reprogram the telemetry device in order to limit the maximum number of times the patient may use the telemetry device to, for example, cause the IMD to release a medicine, or set limits on maximum dosage of medicine or amplitude of stimulation. A programming system 4 may also use device interaction applications for storing patient history information within a patient programming device, or bonding or more generally configuring a patient programming device for use with the patient or a particular IMD 8. Furthermore, once the telemetry device is identified using these techniques, the telemetry device may be used to communicate with and/or program the IMD. Such communication with an IMD 8 may occur at substantially the same time, e.g., using time multiplexing or some other multiplexing scheme, as programming of the patient programming device (i.e., telemetry device 6).

System 2 may offer other potential advantages and uses. For example, a clinician may use one of programming systems 4 to locate an external programming component (e.g., one of telemetry devices 6 or one or more of IMDs 8) that is lost or unavailable. This may be done by discovering all devices in an area and then applying one or more search heuristics to identify the lost device. The programmer system may then send a signal to the lost device in order to cause the lost device to make a noise, flash, or otherwise attract attention to itself. Other examples include notifying a patient when it is time to return to the office, locating a missing patient, enabling features like automatic patient check-in upon arrival at a clinic, determining whether an implanted medical device is safe for use with Magnetic Resonance Imaging (MRI), and so on.

Figure 2:
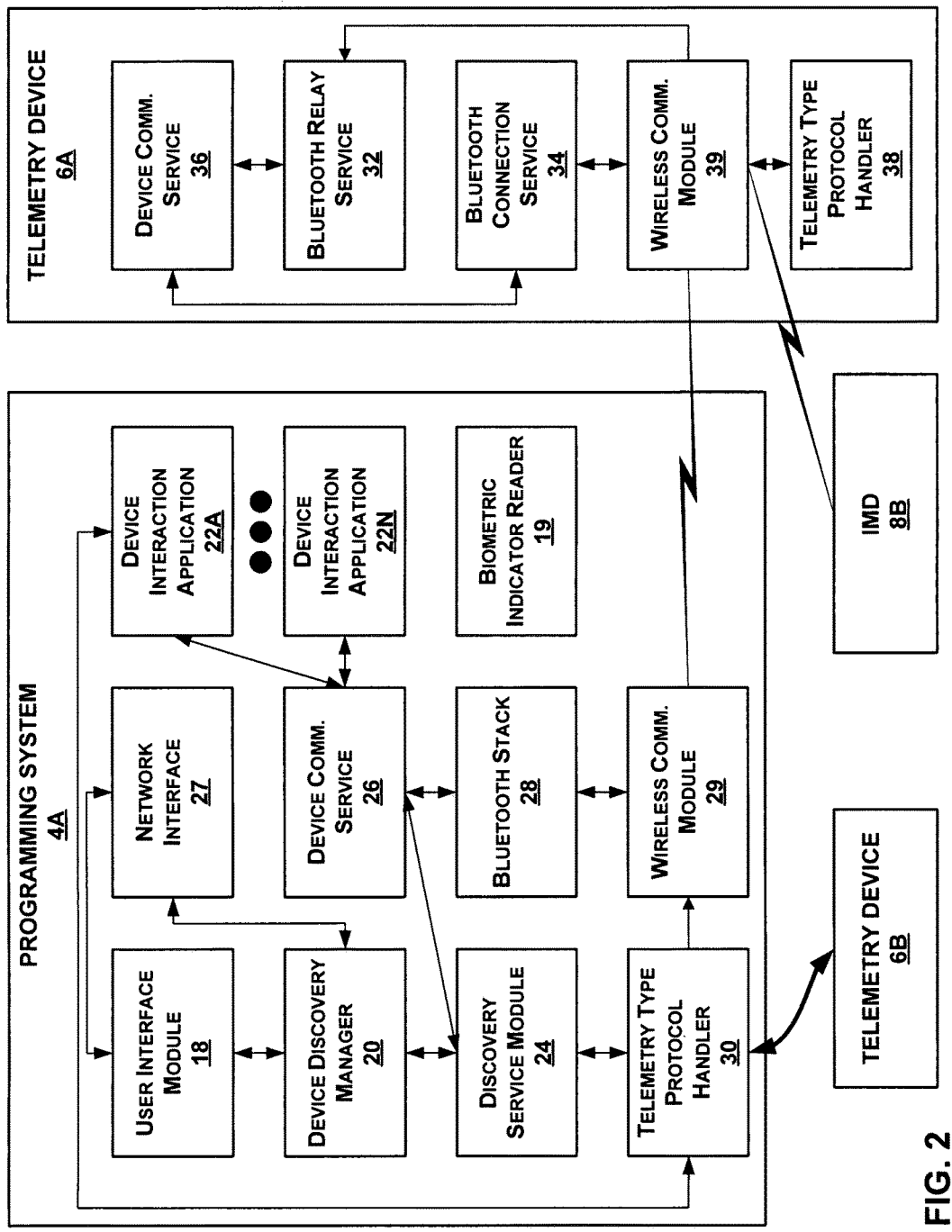
FIG. 2 is a block diagram illustrating an example programming system and telemetry device.

FIG. 2 is a block diagram illustrating example details of programming system 4A and telemetry device 6A. For purposes of explanation, FIG. 2 refers to programming system 4A and telemetry device 6A. However, the following descriptions and examples may be applicable to programming systems 4B through 4N and telemetry devices 6B through 6N.

As illustrated in the example of FIG. 2, programming system 4A includes a user interface module 18, a device discovery manager 20, a set of device interaction applications 22A through 22N (collectively, "device interaction applications 22"), a discovery service module 24, a device communication service 26, a Bluetooth stack 28, a wireless communication module 29, a biometric indicator reader 19, and a telemetry type protocol handler 30. Telemetry device 6A includes a Bluetooth relay system 32, a Bluetooth connection server 34, a device communication service 36, a wireless communication module 39, and a telemetry type protocol handler 38. In general, only one instance of device discovery manager 20 may execute on programmer system 4A.

The components of programming system 4A and telemetry device 6A may interact as follows. Initially, user interface module 18 may present a user interface to a clinician. The clinician may interact with the user interface to instruct programming device 4A to discover available medical devices. When the clinician interacts with the user interface to instruct programming device 4A to discover available medical devices, user interface module 18 may instruct device discovery manager 20 to initiate a device discovery process.

In order to perform a device discovery process, device discovery manager 20 may send a connection request to discovery service module 24. In response to the connection request, discovery service module 24 may discover devices with which programming system 4A may communicate via wired, e.g., serial, links and wireless links. As illustrated in the example of FIG. 2, programming system 4A may communicate with telemetry device 6B via a serial link. For instance, telemetry device 6B may be coupled to and dedicated to use with programming system 4A. In addition, programming system 4A may use wireless communication module 39 to communicate with telemetry device 6A. For example, programming system 4A may use a Bluetooth link to communicate with telemetry device 6A. Discovery service module 24 may use a variety of techniques to discover devices with which programming system 4A may communicate via wired connections. These techniques may include techniques employed in the computer arts to detect new hardware or peripherals.

Discovery service module 24 may use a variety of techniques to discover devices with which programming system 4A may communicate via wireless connections. For instance, discovery service module 24 may first load a telemetry type protocol handler and then find ones of IMDs 8 within range of telemetry device 6A. For example, to load a telemetry type protocol handler, discovery service module 24 may first send a message to device communication service 26 in order to get the types of telemetry supported by device communication service 26. In response, device communication service 26 may respond with a message indicating a start of a list of supported telemetry types. Device communication service 26 may then send one or more messages to discovery service module 24 that specify telemetry types, followed by a message to discovery service module 24 specifying an end to the list of supported telemetry types. After receiving the list of supported telemetry types, discovery service module 24 may send a message to device communication service 26 in order to set a current telemetry type to one of the supported telemetry types. In response, device communication service 26 may send a response to discovery service module 24 confirming the setting of the telemetry type.

To find ones of telemetry devices 6 and IMDs 8, discovery service module 24 may send a message to telemetry type protocol handler 30 instructing telemetry type protocol handler 30 to find devices. If telemetry type protocol handler 30 does not find any devices using the current telemetry type, telemetry type protocol handler 30 may respond to discovery service module 24 with a "device not found" message. Upon receiving a "device not found" message, discovery service module 24 may set the current telemetry type to another one of the supported telemetry types and send another request to telemetry type protocol handler 30 to find devices.

If telemetry type protocol handler 30 detects telemetry device 6A, discovery service module 24 may load a telemetry type protocol handler for telemetry device 6A. To load a telemetry type protocol handler for telemetry device 6A, discovery service module 24 may send a message to communication service 36 in telemetry device 6A in order to get a list of telemetry types supported by telemetry device 6A. In response, communication service 36 in telemetry device 6A may send a list of supported telemetry types to discovery service module 24. Discovery service module 24 may then set the current telemetry type to one of the telemetry types supported by telemetry device 6A. Then, using the current telemetry type, discovery service module 24 may request that telemetry device 6A find devices (including telemetry devices 6 and IMDs 8) that are within range of telemetry device 6A. For example, discovery service module 24 may send a message to telemetry type protocol handler 38 in telemetry device 6A to request telemetry device 6A to find devices. In response, telemetry type protocol handler 38 may send a list of devices within range of telemetry device 6A. For each device within range of telemetry device 6A, telemetry type protocol handler 38 may specify a serial number and a model number of the device. Device discovery service module 24 may then set the current telemetry type to another one of the telemetry types supported by telemetry device 6A. After setting the current telemetry type, discovery service module 24 may request that telemetry type protocol handler 38 use this current telemetry type to find devices.

When discovery service module 24 receives an indication of a new device, discovery service module 24 may send a message to device discovery manager 20 alerting device discovery manager 20 of the newly discovered device. In response to this message, device discovery manager 20 may send a message to discovery service module 24 to request a list of the discovered devices. Discovery service module 24 may provide a list of the discovered devices to device discovery manager 20.

After device discovery manager 20 receives a list of discovered devices, device discovery module 20 may apply one or more search heuristics to the list of discovered devices. The search heuristics used by programming systems 4 may be criteria based on whether or not devices possess specific characteristics, or based on probabilities. Furthermore, the search heuristics may include "historical" search heuristics or "current" search heuristics. Historical search heuristics are search heuristics based on past experience or inputs. In other words, historical search heuristics use probabilities based on past results to sort the directed graph data structure. For example, historical search heuristics may include statically programmed communication configuration information, biological and/or non-biological input, programming system usage patterns (e.g., types of device with which a particular clinician programmer typically interacts), user prompting, signal strength, whether the programming system has a security key to communicate with the device, and so on. In addition, the historical search heuristics may include a search heuristic regarding types of communications link. For example, one search heuristic may favor wired communications links over wireless communications links because of possible interference or to reduce wireless transmissions in a particular area. The programming system may use and/or prioritize these search heuristics dynamically during the search process to prevent the programming system from being slowed by required user/patient response times. Historical search heuristics may be either stored directly on one of programming systems 4 or may be otherwise accessible to the programming system before or at the start of the programming session. This historical search heuristic information may have been collected by and/or stored in one of programming systems 4, one of telemetry devices 6, one of IMDs 8, or a combination of these devices.

"Current" search heuristics are search heuristics based on input provided prior to or during a search. One or more of programming systems 4 or telemetry devices 6 may also present a user interface to prompt a user (e.g., a programming clinician) to optionally enter current search heuristics prior to beginning a search for wireless devices. The current search heuristics may include, but are not limited to, patient identification information, implantable medical device information, type of device that is implanted, type of therapy administered, type of physiological characteristic monitored, identification of one, some of all of the intermediate devices that are to be utilized in the (wireless or partially wired) communication link, a maximum number of hops (e.g., relays) to follow in the communication link, a name of a primary physician or clinic that implanted the device or is treating the medical condition, patient scheduling information either resident or accessible to external programming equipment either before or at the time of the session initiation, usage patterns of the programming system with regard to a particular clinic's set of patients, a cache of previously established communication link information related to the patient, device, clinician, or programming equipment, and so on.

In addition, current search heuristics may include a physical geographic location of a patient. For example, a clinician in one clinic may cause device discovery manager 20 to apply a search heuristic based on geographic locations of IMDs 8. For example, device discovery manager 20 may use a geographic location search heuristic to identify ones of IMDs 8 that are located in a separate clinic, or to exclude IMDs that may be within communication range via a wide area or cellular network, but not in the same clinic as the clinician. Programming system 4A may receive the physical geographic location information via a network interface 27 from Global Positioning System (GPS) location information, cellular control/broadcast channel information, or other location identification system. Alternatively, programming system 4A may use a database to derive the location information. This database may contain a patient's home address, clinic scheduling information (e.g., electronic medical records, electronic health records, etc.), the user or clinician identification information, the identification of one of the external programming component devices (e.g., one of telemetry devices 6) early in a device discovery process, and other types of data that tend to indicate a geographic location of one of IMDs 8. The use of geographic location information may be useful, for example, in situations in which the communication range of a programming system is extensive.

Another search heuristic may include the identification of a dedicated patient programmer device. For example, telemetry device 6A may be associated with a particular patient. In this example, a clinician may cause device discovery manager 20 to apply a search heuristic to filter out connections that do not pass through telemetry device 6A. Furthermore, programming systems 4 or telemetry devices 6 may facilitate storage, retrieval, and data entry of communication, security, and access control information needed to safely utilize patient programmer devices for an external programmer session. Programming systems 4 may also dynamically adjust to situations where a patient might refuse session establishment through his or her patient programmer device, either permanently or temporarily. In other words, a clinician may cause device discovery manager 20 to apply a search heuristic to filter out communications links through a patient programmer device in order to more easily identify an alternative communications links to a patient's implanted medical device.

Conversely, programming systems 4 may apply a search heuristic to filter out communication links through devices that are not currently configured to allow session establishment. For instance, programming system 4 may apply a search heuristic to filter out communication links through devices that are not currently bonded to particular ones of IMDs 8 or that require user input to establish a session with one of IMDs 8. As an example, programming system 4 may apply a search heuristic constraining discovered devices to one or more devices for which a proximity-based consent method, as described below, has been performed to allow communication with the device.

The user may choose not to enter current search heuristics. Moreover, the user may choose to enter the current search heuristics after the programming system has begun the search or may use the current search heuristics to narrow the results after the programming system has completed the search.

Because device discovery manager 20 may apply a large number of search heuristics, interface module 18 may provide a user interface that enables a clinician to prioritize the search heuristics. Alternatively, device discovery manager 20 may automatically adjust relative priorities of the search heuristics as appropriate for fine tuning the search process upon the initiation of successive communication sessions. Automatic prioritization within and across patient profiles may serve as a method to improve the efficiency at which device discovery manager 20 identifies a desired one of IMDs 8.

One of programming systems 4 may also discover and sort devices in multi-hop communication networks where one or more of the hops includes all or part of an implantable multi-hop network consisting of multiple ones of IMDs 8 that communicate either similarly or dissimilarly from the other communication nodes that may be part of the external programming component network. Support for this infrastructure may include, but not be limited to, communicating with one or several implantable sensors that can only be communicated with by communicating through a master implantable medical device that relays information to or from the sensor and to or from one of programming systems 4.

Because differences may exist between communication methods used by IMDs 8, device discovery manager 20 may offer suggestions to the user that may accelerate a search process or bring additional ones of telemetry devices 6 or IMDs 8 into range. These suggestions may include, but are not limited to, a suggestion that a programming device or component be properly positioned with regard to one of IMDs 8 in order to facilitate a near-field wireless communication, a suggestion that the clinician should enable a required one of telemetry devices 6 for device discovery and/or data reception, and other suggestions. In addition, these suggestions may provide communications-related security information or may prompt a user to invoke an action that activates a secure communications session.

Programming systems 4 may load one or more search heuristics related to a patient or clinician when the patient or clinician identifies himself or herself by providing a biometric indicator to biometric indicator reader 19 of programming systems 4. For example, a patient or a clinician may swipe a finger over a fingerprint scanner or look into a retina scanner. Loading the search heuristics in response to identifying a patient or clinician using a biometric indicator may save time over manual data entry of a patient's or clinician's name, identification number, etc. This may be especially important in the context of an emergency room.

A clinician using programming system 4A may interact with user interface to select one of the discovered devices. When the clinician selects one of the devices, device discovery manager 20 may launch one or more device interaction applications associated with the selected device.

Device discovery manager 20 may launch the selected device interaction applications in a secure manner without the need to re-establish connections. In order to launch the selected device interaction applications in a secure manner without the need to re-establish connections device discovery manager 20 may send a message instructing discovery service module 24 to request a connection hand off. Upon receiving this request, discovery service module 24 may send a connection request message to device communication service 26. Discovery service module 24 may start a communication service login sequence. For example, a clinician may provide a username and password. If the login sequence is successful, discovery service module 24 may send a message instructing device communication service 26 to set handoff data. The handoff data may include device serial number, device mode number, wired connection string, telemetry device name, telemetry device wireless address, telemetry type, security information, and so on. Device communication service 26 may then send a message to discovery service module 24 to inform discovery service module 24 that device communication service 26 successfully set the handoff information. This message may also include a handoff connection ID. After receiving the handoff connection ID, discovery service module 24 may send a message to device communication service 26 to disconnect and device communication service 26 may respond with a message indicating successful disconnection. After receiving the message indicating successful disconnection from device communication service 26, discovery service module 24 may send a message to device discovery manager 20 to inform device discovery manager 20 that connection handoff is complete. When device discovery manager 20 receives this message, device discovery manager 20 may generate a "start handoff complete" event. If device interaction application 22A is associated with the selected device, device discovery manager 20 may then start device interaction application 22A, passing the handoff connection ID as input to device interaction application 22. Subsequently, discovery service module 24 may clean up (e.g., terminate) any connections for which a connection handoff was not performed. After cleaning up may unused connections, device discovery manager 20 may terminate.

After one of device interaction applications 22 starts, the device interaction application may create a remote connection to the device and begin a session by sounding a non-critical alarm on the device. To create a remote connection to the device, the device interaction application may send a message to device communication service 26 to start a connection. Device communication service 26 may then begin a communication service login sequence. If the login sequence is successful, the device interaction application may send a request to device communication service 26 to get handoff data associated with the handoff connection ID. In response to the request for handoff data, device communication service 26 may send a message to the device interaction application that includes the handoff data (e.g., device serial number, device model number, wired connection string, telemetry device name, telemetry device wireless address, telemetry type, etc.) After the device interaction application receives the handoff data, the device interaction application may send a request to device communication service 26 to connect to a known device. This message may specify a device name, a device address, and a device service name.

Upon receiving a request to create a connection to a known device, device communication service 26 may send a request to Bluetooth stack 28. This message creates a new Bluetooth stack. Furthermore, Bluetooth stack 28 may use wireless communication module 29 to send a message to wireless communication module 39 on telemetry device 6A. The message requests the start of the establishment of a Bluetooth connection. When wireless communication module 39 receives the message, wireless communication module 39 may forward the message to Bluetooth connection service 34. When Bluetooth connection service 34 receives the request, Bluetooth connection service 34 may send a message to device communication service 36 to connect. Bluetooth connection service 34 may then send a message to Bluetooth stack 28 that informs Bluetooth stack 28 of the end of Bluetooth connection establishment. After receiving this message, Bluetooth stack 28 may send a message to device communication service 26 with a device/stream handler of the established Bluetooth connection. In response, device communication service 26 may send a message to Bluetooth stack 28 to discover services provided by Bluetooth stack. When Bluetooth stack 28 receives this request, Bluetooth stack 28 may respond with a message to device communication service 26 that informs the device communication service that Bluetooth stack 28 has completed the discovery of the services. Device communication service 26 may then send a message to Bluetooth stack 28 to connect to one of the services. In response, Bluetooth stack 28 may send a message to device communication service 26 indicating that connection to the service is complete. At this point, device communication service 26 may send a message to one of device interaction applications that indicates that the connection attempt to the known device was successful.

To begin a session, one of device interaction applications 22 may use the device/stream handler to send a request to device communication service 36 on telemetry device 6A to set a telemetry type to a current telemetry type for the device. In response, device communication service 36 may send a message to the device interaction application indicating that the device communication service successfully set the telemetry type. The device interaction application may then send a message to telemetry type protocol handler 38 to test a non-critical alarm. Telemetry type protocol handler 38 may then respond with a confirmation of the test of the non-critical alarm.

Figure 3:
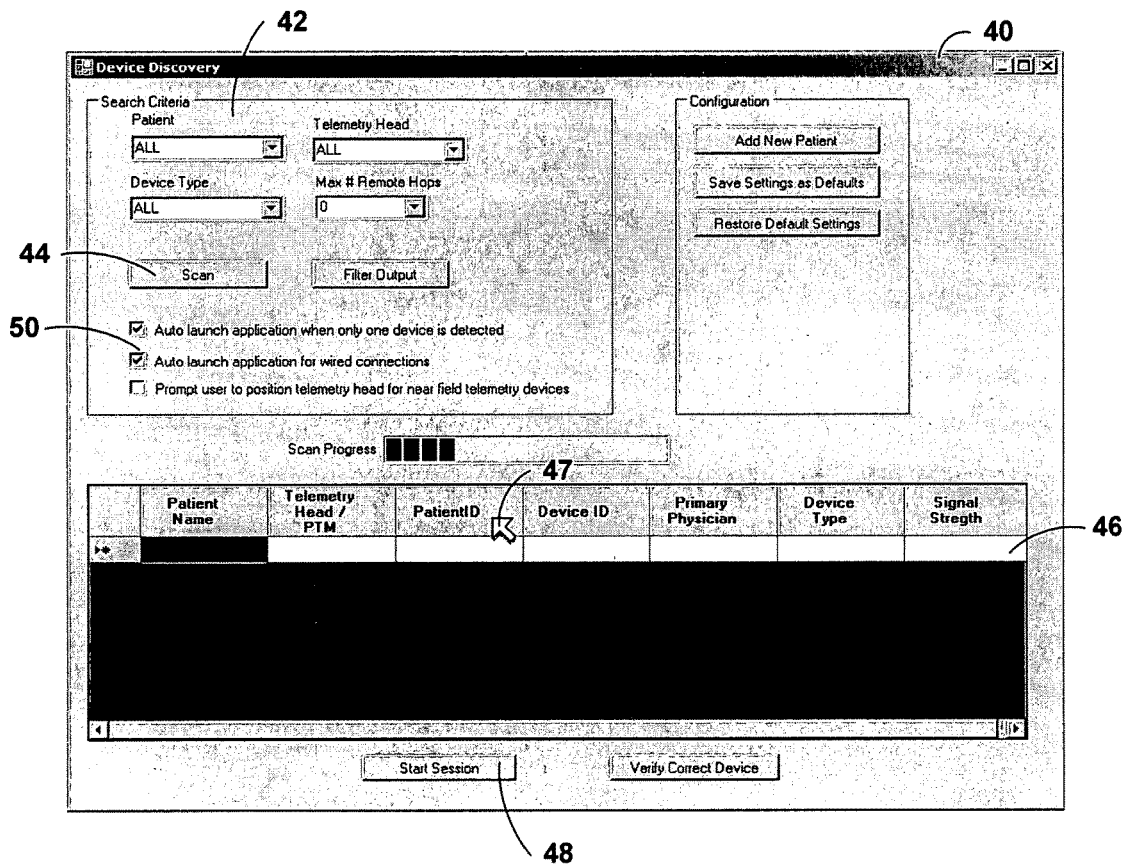
FIG. 3 is a screen illustration showing an example search interface presented by a programming system.

FIG. 3 is a screen illustration showing an exemplary search interface 40 presented by one of programming systems 4. As illustrated in the example of FIG. 3, interface 40 includes a set of drop boxes 42 that allow a clinician to input four current search heuristics (labeled "Search criteria" in search interface 40). These search heuristics allow a clinician to select a patient, to select one of telemetry devices 6, to select a device type, and to select a maximum number of remote hops.

When a clinician opens search interface 40, the programming system may automatically begin a search to identify a desired one of IMDs 8. In searching for the desired IMD, the programming system may apply the search heuristics entered in drop boxes 42 and historical search heuristics. Furthermore, when the clinician clicks a "Scan" button 44 in search interface 40, the programming system may apply the search heuristics specified in drop boxes 42 to known devices, devices already discovered, and any devices that the programming system may discover as the programming system continues the search. If, based on the search heuristics, the programmer system identifies a device that is likely to be the desired IMD or telemetry device, the programmer system displays information about the device in a table 46. The clinician may then select a device displayed in table 46 and initiate a communication session with the selected device by selecting a "Start Session" button 48.

Search interface 40 also includes check boxes 50 to control whether the programming system automatically launches a device interaction application to interact with the selected IMD. For example, search interface 40 includes a first check box to auto launch ones of device interaction applications 22 when only one device is detected and a second check box to auto launch ones of device interaction applications 22 for wired connections.

Table 46 includes a set of column headers. In the example of FIG. 3, table 46 includes the column headers "Patient name," "Telemetry Head/PTM," "Patient ID," "Device ID," "Primary Physician," "Device Type," and "Signal Strength." A clinician may use a pointer 47 to click on any of these column headers. When the clinician clicks on one of the column headers, the programmer system providing interface 40 may re-sort table 46 according to the data in the column associated with the clicked column header. For example, cells in the column associated with the "Patient ID" column header may specify patient identification numbers associated with individual patients. If a clinician uses pointer 47 to click on the "Patient ID" column header, the programmer system may re-sort table 46 such that the data in the rows of table 46 are organized by increasing (or decreasing) patient identification number.

Figure 4:
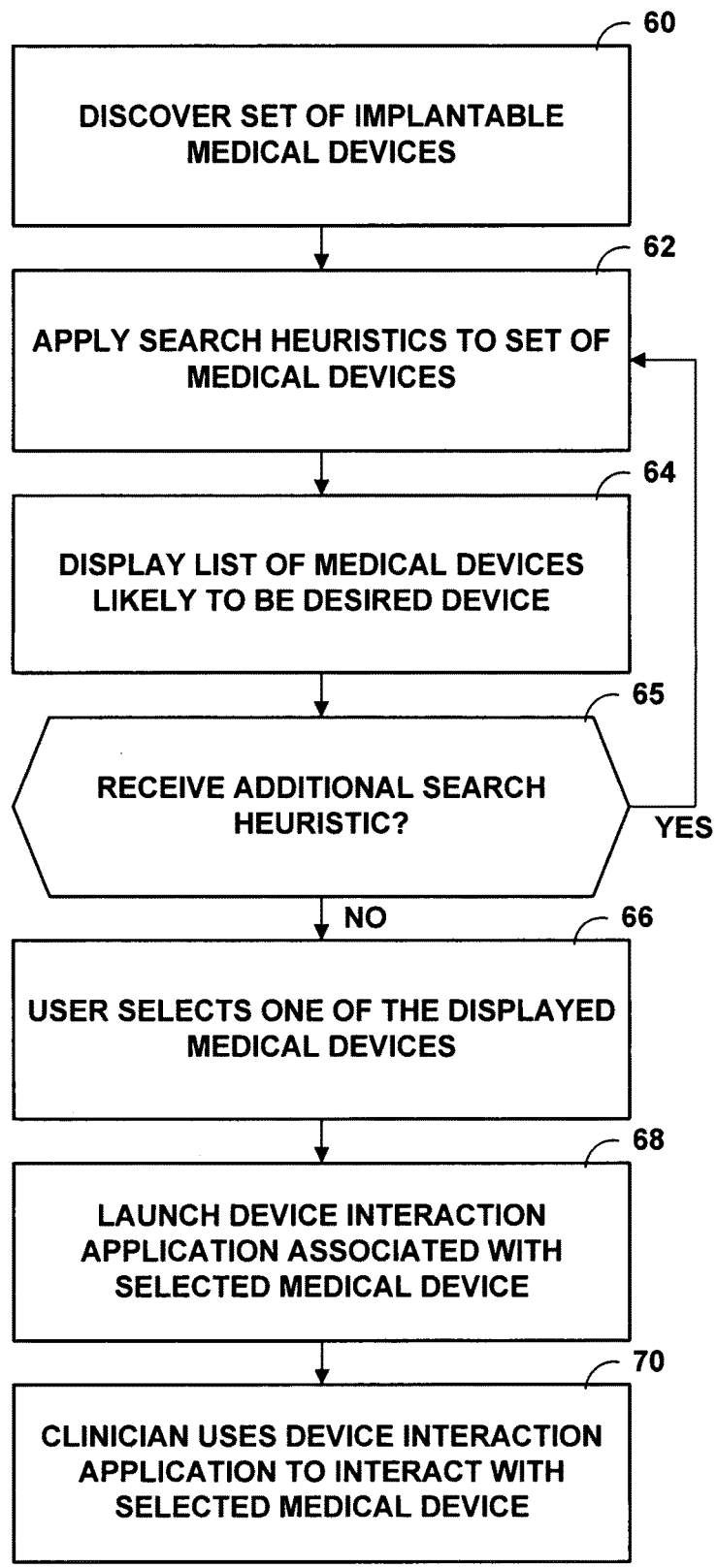
FIG. 4 is a flow diagram illustrating example operation of a programming system.

FIG. 4 is a flowchart illustrating an example operation of one of programming systems 4. For purposes of explanation, reference is made to programming system 4A in regards to FIG. 4. However, any of programming systems 4 may perform this exemplary operation. A computer-readable medium comprising instructions may cause programmable processors in programming systems 4 to perform this operation, or provide any other functionality described herein.

Initially, programming system 4A discovers a set of medical devices, e.g., telemetry devices 6 or IMDs 8 (60). As programming system 4A discovers the set of medical devices, programming system 4A may build a directed graph data structure that identifies devices with which programming system 4A may communicate. Programming system 4A may discover the set of medical devices using one or more wired or wireless communication links.

After discovering the set of medical devices, programming system 4A may apply search heuristics to the set of medical devices to identify one or more of the medical devices in the set that are likely to be a medical device with which a clinician desires to interact (62). In some circumstances, programming system 4A may apply the search heuristics prior to beginning discovery of the set of medical devices. Thus, steps (60) and (62) may be reversed. In these circumstances, programming system 4A may instruct discovered devices not to return further devices that to not match the search heuristics. Programming system 4A may then display a list of medical devices that programming system 4A identified as likely to be the desired medical device (64).

After programming system 4A displays the list of medical devices, programming system 4A may receive one or more additional search heuristics (65). If programming system 4A receives one or more additional search heuristics ("YES" of 65), programming system 4A may apply these additional search heuristics to the set of medical devices already listed (62), and so on. If, at this point, programming system 4A does not receive any additional search heuristics ("NO" of 65), the clinician may select the desired medical device from the displayed list (66). When the clinician selects the desired implantable medical device from the displayed list, programming system 4A may launch one or more device interaction applications associated with the selected medical device (68). The clinician may then use the device interaction applications to interact with the selected medical device, e.g., to program the device or retrieve data from the device (70).

A connection that exists between one of programming systems 4 and one of IMDs 8 may be divided into two logical parts: (a) a private, authenticated non-proprietary link between one of programming systems 4 and one of telemetry devices 6, and (b) a private, authenticated, and access controlled proprietary link between the one of telemetry devices 6 and the one of IMDs 8. As long as access control is applied to the proprietary link when programming the IMD, there may be no need to apply access control to the non-proprietary link to the telemetry device as long as telemetry device is private and authenticated. In other words, programming systems 4 may inherit the ability access IMDs 8 from telemetry devices 6 when the telemetry device is private and authenticated, or access control is otherwise applied to the proprietary link between the telemetry device and IMD.

Programming systems 4, telemetry devices 6, and IMDs 8 may implement access control, privacy, and authentication on the non-proprietary link by either using a direct, wired connection (e.g. USB) or via bonding. As discussed above, the term "bonding" refers to configuring two devices with a shared key. The devices use the shared key when securely communicating with each other using one or more wireless links. Once two devices establish a bond, there may be no need to enable the telemetry device for discovery that makes the link more secure. Without creating the bond, the telemetry device might need to temporarily enable device discovery so that one of programming systems 4 may connect to the telemetry device.

Privacy, authentication, and access control of the proprietary link may be accomplished differently based on whether the IMD communicates via a near-field or far-field link, and whether the connection is being established through a telemetry device that is bonded to the IMD or a telemetry device that has not been bonded to the IMD.

However, in some embodiments, any communication to an IMD (other than direct communication from a bonded telemetry device) involves some sort of action by the patient to allow access to the IMD. For example, these actions may include allowing one of telemetry devices 6 into the close proximity of the patient. In general, patients would only allow one of telemetry devices 6 within their close proximity when they consent to the one of telemetry devices 6 communicating with their IMDs. IMDs 8 may detect close proximity to a patient in a variety of ways. These ways may include placing one of telemetry devices 6 in the patient's hand and detecting the patient's heart rate. The telemetry device may then transmit the detected heart rate to the IMD. The IMD may also measure the patient's heart rate. If the IMD determines that the patient's heart rate as measured by the IMD matches the heart rate transmitted to the IMD by the telemetry device, the IMD may establish a secure connection to the telemetry device because if the telemetry device has detected the patient's current heart rate, the patient must have allowed the telemetry device into his or her close proximity.

In another example, one of telemetry devices 6 and one of IMDs 8 may include accelerometers. When a clinician wants the telemetry device to communicate with the IMD, the clinician may tap the telemetry device against the patient's body near the site of the IMD. When the clinician taps the telemetry device against the patient's body, the accelerometers in the telemetry device and the IMD may detect the force of the tapping. The telemetry device may transmit signals to the IMD that indicate the force of the tapping as perceived by the accelerometer in the telemetry device. When the IMD receives these signals, the IMD may determine whether the force of the tapping detected by the accelerometer in the telemetry device corresponds to the force of the tapping detected by the accelerometer in the IMD. If the force of the tapping detected by the accelerometer in the telemetry device corresponds to the force of the tapping detected by the accelerometer in the IMD, the IMD may allow a secure connection with the telemetry device. In other embodiments, a predetermined pattern of tapping, known by the patient and/or clinician, may be detected by the IMD alone. The IMD may allow secure communication with a proximate telemetry device in response to detecting the authorization in the form of the tapping pattern.

In a third example, when a clinician wishes to communicate with one of IMDs 8 in a patient, the clinician may insert a needle into a septum of the IMD. A septum of an IMD may be an aperture in the IMD that is close to a patient's skin. When the clinician inserts the needle into the septum, the IMD may detect the presence of the needle. The presence of the needle in the septum may be detected, for example, by a strain gauge coupled to the septum. When IMO detects the presence of the needle, the IMD may allow a secure connection with a telemetry device.

In a fourth example, one of telemetry devices may include a magnet and an IMD may include a magnetically activated switch. When a clinician holds the telemetry device close to the IMD, the magnet in the telemetry device activates the magnetically activated switch in the IMD. When the magnetically activated switch in the IMD is activated, the IMD may allow a secure connection with the telemetry device.

In addition to these proximity-based mechanisms, a patient may perform one or more other actions to allow communication to one of IMDs 8 that is implanted in the patient. These other actions may include accepting the request from a programming system to connect through a telemetry device to its bonded far-field IMD via some sort of user interaction on the telemetry device; using the trusted third party mechanism for establishing a session with the (far-field) IMD; and unlocking the back door method of initiating a session with the (far-field) IMD. In another example, a patient may be issued a smartcard that includes an encryption key recognized by an IMD implanted in the patient. Furthermore, a telemetry device, clinician programmer, or other device of a programming system may include a housing that accepts the smartcard. When the patient wishes to allow communication to the IMD, the patient, clinician or other caregiver may insert the smartcard into the housing of the telemetry device, clinician programmer, or other device of the programming system. The device may then read the smartcard and use the encryption key of the smartcard to communicate with the IMD.

IMDs 8 may be able to communicate in a non-secure fashion for communicating information that identifies the IMDs, for establishing communication links, and for some other purposes. However, IMDs 8 might not apply changes to its internal programs or parameters without the establishment of a secure session.

The following table summarizes exemplary access control mechanisms that may be required for establishing the specified communication link.

| Telemetry Device type | IMD type | Connection Establishment Steps |
|---|---|---|
| Wireless untethered telemetry device bonded to programming system | Near field device | Session is established by just placing untethered telemetry device in vicinity of the IMD. |
| Wireless untethered telemetry device bonded to programming system | Far field device | Unlocking proprietary link with help from trusted $3^{rd}$ party or backdoor mechanism. |
| Wireless patient programming device (bonded or not bonded to IMD) or wireless untethered telemetry device not bonded to programming system | Near field device | Session established by user (1) enabling discovery on patient programming device; (2) Placing the patient programming device in the vicinity of the IMD. |
| Wireless patient programming device (bonded to IMD) | Far field device | Since patient programming device has been bonded to IMD, it knows how to connect securely. However, before it lets any programming system that asks it to access the device, the IMD requires user acknowledgement to accept the connection request. |
| Wireless patient programming device (not bonded to IMD) | Far field device | In order to be able to use another patient's patient programming device to connect to a non-bonded device: (1) need to enable the patient programming device to accept a pass through connection to an unbonded device; (2) unlock the proprietary link with help from trusted $3^{rd}$ party or backdoor mechanism. |
| Wireless untethered telemetry device bonded to programming system or wired untethered telemetry device | Far field device | Session established by user (1) unlocking the proprietary link with help from trusted $3^{rd}$ party or backdoor mechanism. |
| Wired patient programming device (bonded to IMD) | Near field or Far field device | No user interaction required after connecting cable to allow communication access of programming system to IMD. |
| Wired patient programming device (not bonded to IMD) | Far field device | Session established by user (1) unlocking the proprietary link with help from trusted $3^{rd}$ party or backdoor mechanism. |
| Wired patient programming device (not bonded to IMD) | Near field device | Session is established by just placing patient programming device in vicinity of the IMD. |

For example, device communication service 26 may unlock a "backdoor" method for unlocking a secure far-field link to the device or use a mutually trusted third party to the device. "Backdoor" methods may include a device of some short range (e.g., telemetry device 6A) used to indicate that the person unlocking the backdoor has been granted access to the personal space of the patient. Forms of trusted third party mechanisms for unlocking a secure far-field link to the device may include, secure ID card, a USB device, a sticker containing security information that is kept in a patient's file in a clinic, a bonded patient programmer device that grants approval for making the connection, a call into a field support technician, or a secure vendor server.

Figure 5:
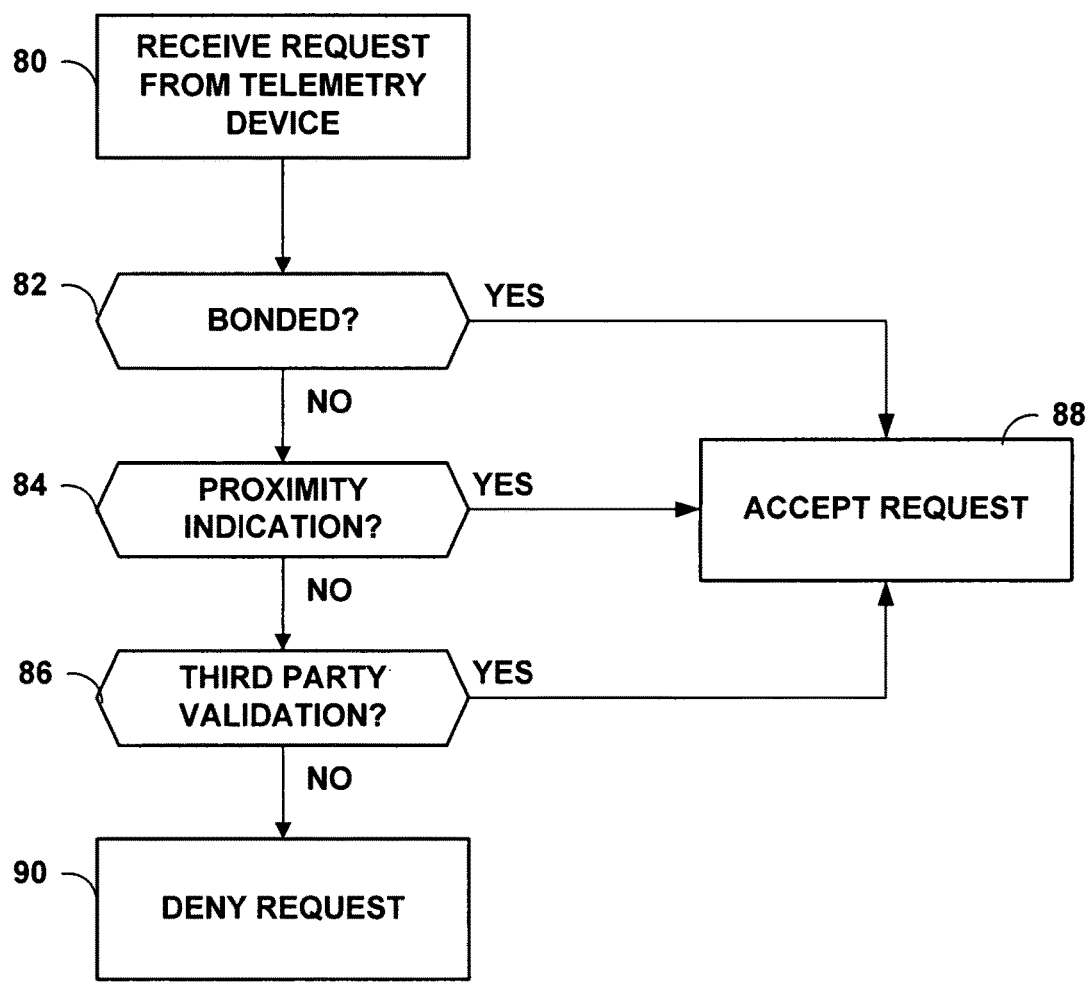
FIG. 5 is a flow diagram illustrating example operation of an implantable medical device to determine whether to allow communication with a telemetry device.

FIG. 5 is a flow diagram illustrating example operation of an IMD 8 to determine whether to allow communication with a telemetry device 6 and, in some cases, thereby allow communication with a programming system 4 via the telemetry device. According to the example, an IMD 8 receives a request for communication from a telemetry device 6 (80). Telemetry device 6 may provide the request in response to a request from a programming system 4, either during or after the discovery process described above.

If the telemetry device 6 is already bonded to the IMD 8 (82), e.g., is a dedicated patient programming device for the IMD or otherwise possesses a key for communication with the IMD, the IMD 8 may accept the communication request (88). The IMD 8 may then allow the telemetry device 6 to, for example, communicate programming commands to the IMD. The programming commands communicated to the IMD 8 may have been received by the telemetry device 6 from a programming system 4, and communicated to the IMD without the IMD separately authenticating the programming system. In this manner, the programming system may inherit the bond or other authentication (described below) of the telemetry device.

If the telemetry device was not previously bonded (82), IMD 8 may determine whether it has received a valid proximity indication, indicating that the patient consents to communication with the telemetry device 6 (84). Examples of such proximity indications, including use of near-field telemetry, accelerometer detected tapping patterns, or magnet activation, are described herein. If IMD 8 has received a proximity indication (84), the IMD may allow communication with the telemetry device (88). If not, the IMD may deny the communication request (90).

The IMD may also determine whether it has received a trusted third party validation as described herein (86), e.g., a key communicated from the telemetry device that was included on a smart card in the possession of the patient. If the IMD has received trusted third party validation, the IMD may accept the communication request (88). If not, it may deny the request (90).

In example embodiments, a Bluetooth link may be used to facilitate communication between programming systems 4 and medical devices, e.g., telemetry devices 6. There are three levels of security that may be addressed with regard to the wireless Bluetooth link. These levels of security include access control, data privacy, and device authentication.

In theory, the Bluetooth communication protocol has all the necessary features to provide for secure and private communications (authentication, authorization, and encryption). While Bluetooth does provide authentication support, it is not implemented on each packet or on each message (i.e. no packet authenticity). However, because a packet is only valid for the time-slot in which the packet is sent, it is difficult to manipulate the packets unless the attack also is applied to the time synchronization protocol.

The Bluetooth protocol supports data encryption. Programming systems 4, telemetry devices 6, and IMDs 8 may enable the optional encryption to make the link secure. Further, the Bluetooth protocol also supports authentication via personal identification number (PIN) codes. The users on both ends may utilize an agreed upon (variable-length) PIN code to serve as an input to a hash algorithm used for message authentication. This PIN code may be a variable-length sequence of characters. It may be desirable to force the user to use PIN codes that include sixteen characters instead of PIN codes that only include four characters because it may be easier to compromise shorter PIN codes. It may also be important to randomly generate PIN codes so that the PIN codes vary widely from one pair of devices to the next. Therefore, one of the two communicating devices in system 2 may randomly generate a PIN code when the two are bonded/paired.

In a typical scenario, communicating Bluetooth devices are owned by the same user. In this scenario, there is not much concern that a malicious party may tamper with the bonding information on either side of the link. However, in an environment such as system 2 where the same individual does not own both of the communicating devices, it is possible that that bonding information on one of the devices gets deleted on one of the devices, making the connection less secure. This can be handled by the application checking to ensure that a bond exists with a device that established a connection before continuing to communicate with it.

One additional issue involves device interaction applications that run on non-proprietary hardware. When a device interaction application runs on non-proprietary hardware, it may be insufficient to validate that the patient programming device is talking to a trusted device, but also to a trusted application and user. To solve this problem, either the Bluetooth link to the telemetry device or a Bluetooth link to the patient's device may be locked down using secret data supplied by a trusted third party.

In order to prevent malicious activity from being completed by someone who obtains a patient programming device and a copy of programming software, the programming software may rely on a trusted third party (e.g. a manufacturer server) to validate a user prior to giving the user access to the communication link. For hardware supplied by a vendor other than the manufacturer, a new, randomly generated PIN code may be used for each session.

Because the Bluetooth pairing only validates that an authorized device is being connected and not necessarily the user or the application, Bluetooth alone does not provide the necessary authentication checks that would be necessary when the programming software is allowed to run on non-proprietary hardware. To solve this problem, a trusted third party in the form of a secure ID card, or a secure server may be used to provide the additional security. Furthermore, if a first device initially uses a wireless link to communicate with a second device and a wired link is subsequently established, the first device and the second device may begin communicating using the wired link. This is because the wired link may be faster and more secure.

As in any wireless protocol, Bluetooth is susceptible to jamming that prevents the link from being used for communication. For this reason, an alternative wired link may allow this more reliable communication when necessary. The wired link might also be required in environments where radio transmission is not allowed.

The Bluetooth specification makes a suggestion to use application-level key agreement software with longer (up to 16 octets) PIN codes. The PIN code need not be entered physically to each device of the connection. Rather, the devices may use a secure key exchange algorithm to exchange the PIN codes. For example, the device may use the Diffie-Hellman key algorithm to exchange the PIN codes. However, secure key exchange algorithms may be computationally intensive. Moreover, using application-level key agreement software does not make the connection more secure. Rather, application-level key agreement may simplify the initial bonding step by eliminating the need for a user to be involved with transferring the PIN codes. As an alternative to Diffie-Hellman, the application-level key may be transferred using a wired USB link.

In order to meet the customer needs of both convenience and security, while realizing that the threshold for each of this may differ from one customer to the next, four different security levels may be implemented for securing the connection between the programming device and patient programming device. All security levels should include the features of enabling the protocol stack encryption, and authentication features, and providing some sort of user detectable indication (sound, visual, vibrate) that a communication session is being requested or established and that the user is connecting to the intended device.

The first of these security levels would allow links to be established between a telemetry device and a programming system without first establishing a PIN code. When this is not done, the initial link establishment can be overheard, opening the session to potential eavesdropping. Another potential problem might be connecting with the wrong device (i.e. one pretending to be the desired device). In this first security level, the risk of these vulnerabilities might not be eliminated, but reduced by one or more application-level design steps. First of all, in this and all other modes, a patient programming device does not configure itself to be discoverable by other devices (except for briefly making itself bondable to enable security level 2. Instead, some sort of user intervention would be required to allow a programming system to be able to start a session with an IMD, such as those described above, e.g., tapping, magnets, or the like. This prevents a connection from being established with a patient's IMD without the patient's knowledge.

The feature where a device is not discoverable without user intervention may be applied to all security levels. The feature where user intervention is required for establishing any connection to the patient programming device may not be as necessary for the higher security levels. User intervention may also be used to establish a connection between the third and fourth levels of security The second security level and all higher security levels require that a PIN code be used to bond the programming system and patient programming device devices. The application-level software may require that the maximum sixteen character PIN code be used for maximum security, and may allow/enforce the use of both digits and characters to increase the range of values that can be used. System 2 may disallow the use of special (e.g. punctuation) characters because there have been reports of problems with some protocol stacks processing these special characters.

As part of the bonding process, programming systems 4 may use application-level exchange that also passes the name and address of the device being bonded with. This may then eliminate the need to have to discover the presence of the device in order to establish a connection. This means in the second security level, the only time that a patient programming device needs to be made discoverable is during the time that this initial bond is established. The need to make the device discoverable could be eliminated by having the user manually enter the address and device name, but since entry of the address and device name may already occur by the first security level for link establishment, an additional inconvenience could be eliminated during at the time the device needs to be made discoverable for this mode of operation.

The third security level differs from the second security level in that the device may never need to be made discoverable, since a wired link is used to transfer the device address and name that is required for establishing a bond. The third security level also goes one additional step by requiring an application-level password to be exchanged along with the wired bonding information. Because the application-level password and wired bonding information is potentially passed via a wired connection, the information can be randomly determined without user intervention. Note that the user could also append the application-level password and wired bonding information to the information entered by the user at the second security level.

Because the device was never made discoverable, an added convenience of the third security level over the second security level is to be able to relax the need for user intervention upon session establishment. Since the patient programming device information was never made public, it might be unnecessary to reconfirm the connections made between these two devices.

Finally, the fourth security level may be identical to the third security level, but may add back the need for user confirmation for session establishment.

| Security Level | Always Non-discoverable | Non-discoverable except when manually enabled during connection establishment | Non-discoverable except when manually enabled during bonding. | Visual/audible notification when session established | Encryption enabled | User intervention required to start session | PIN Code bonding required | PIN Code established via wireless link and manual PIN Code Translation | PIN Code and/or password established via wired link | Application level password required to communication via an established link | Manual confirmation required before communication can commence |
|---|---|---|---|---|---|---|---|---|---|---|---|
| 1 |   | X |   | X | X | X |   |   |   |   |   |
| 2 |   |   | X | X | X | X | X | X |   | X |   |
| 3 | X |   |   | X | X | X | X |   | X | X |   |
| 4 | X |   |   | X | X | X | X |   | X | X | X |

It should be noted that the four security levels discussed in the preceding paragraphs and table are exemplary security levels. Many other security levels, and the use fewer or greater security levels, are possible and within the scope of this disclosure.

An additional alternative may be the use of fixed or random PIN codes. Design simplification may be gained using a fixed PIN. While the use of random PIN codes may provide a method to address a situation where a PIN code becomes known, the use of random PIN codes does not otherwise make the communication link any less secure.

Another additional safeguard may comprise preventing bonding in the presence of other discoverable devices. However, an educated eavesdropper may disable his or her own discoverability to gain to override this safeguard. Therefore, this additional safeguard may not increase the worst case security scenario and does not add any additional convenience to the user, so is likely not worth implementing.

Yet another safeguard may comprise application-level verification of bonding. An application may check to ensure that a (local) bond exists with a device that established a connection before continuing to communicate with the device. This is relatively simple and adds an additional check to make sure the device has not been tampered with.

Bluetooth may be used to implement a multi-hop network of remote telemetry devices (e.g. from a waiting room to a clinician programmer via multiple hops). However, an 802.11-based network solution may also provide a multi-hop mesh network of programming systems, telemetry devices, and medical devices. These and other communication protocols may be used.

In some example configurations of system 2, one or more telemetry devices 6 may initially be coupled to one or more programming systems 4 using detachable cables. While one of telemetry devices 6 is coupled to one of programming systems 4, the programming system may only discover the telemetry device. That is, the programming system may be configured to search only for devices that are physically coupled to the programming system. Furthermore, after the programming system discovers to telemetry device, the programming system may use the cable to receive information about the telemetry device or a particular IMD. For example, the programming system may receive security information from the telemetry device, e.g., facilitating a wireless communication session between the programming system and the telemetry device and, through the telemetry device, with the IMD.

Subsequently, a clinician may detach the telemetry device from the programming system and, for example, carry the telemetry device to an examination room where an implantable medical device is located. The clinician may then, using the programming system, send a wireless communication to an IMD via the untethered telemetry device.

Various embodiments of the invention have been described. For example, embodiments in which a programming system discovers a plurality of medical devices, e.g., using a device discovery manager, have been described. Embodiments in which a number of devices discover other devices that they are able to communicate, and share information regarding devices available for communication to created a multi-hop directed graph data structure have also been described. Embodiments in which a number of devices discover other devices may facilitate distributed discovery of medical devices, and may include a distributed set of device discovery managers.

Various modifications may be made to the described embodiments without departing from the scope of the claims. These and other embodiments are within the scope of the following claims.

The invention claimed is:

1. A programming system comprising:
a discovery service module that wirelessly broadcasts a request for medical devices within range of the programming system to identify themselves, and receives individual responses to the request from each medical device in a set of medical devices to discover each medical device in the set of medical devices, the set of discovered medical devices including at least two medical devices; and
a device discovery manager that applies one or more search heuristics to the set of discovered medical devices to identify a subset of one or more medical devices in the set, identifies one of the medical devices from the subset, selects one or more device interaction software applications, based on the identification of the medical device from the subset, from among a plurality of device interaction software applications, and initiates a wireless communication session with the identified one of the medical devices from the subset by launching the selected one or more device interaction software applications to facilitate user interaction with the identified medical device via the programming system,
wherein the one or more search heuristics applied by the device discovery manager to identify a subset of one or more medical devices in the set comprises at least one or more of a group consisting of:
a telemetry device type;
a telemetry device configuration;
telemetry devices to use for communication;
probabilities based on past results;
whether additional actions need to be performed in order to establish a connection; and
a maximum number of hops to follow in a mesh network for establishing a connection.

2. The system of claim 1, wherein the device discovery manager applies one or more of the search heuristics to already discovered medical devices in the set while the discovery service module is discovering additional medical devices in the set.

3. The system of claim 2, wherein the programming system further comprises:
a database that stores search heuristics associated with a patient; and
a biometric reader to read a biometric indicator of the patient,
wherein the device discovery manager applies the search heuristics associated with the patient when the biometric reader reads the biometric indicator of the patient.

4. The system of claim 1, wherein the programming system further comprises an interface module that presents a user interface that prompts the user to enter one or more of the search heuristics.

5. The system of claim 1,
wherein the programming system further comprises a network interface to receive geographic location information regarding the one or more medical devices in the set, and
wherein the device discovery manager applies the geographic location information as an additional one of the search heuristics to identify the subset of the one or more medical devices.

6. The system of claim 1, wherein the device discovery manager automatically selects the one or more device interaction software applications associated with the medical device identified from the subset.

7. The system of claim 1, wherein the device discovery manager automatically launches the selected one or more device interaction software applications associated with the medical device identified from the subset.

8. The system of claim 1, wherein the programming system further comprises an interface module that presents a first list of one or more medical devices in the subset and that receives an indication from the user regarding which one of the one or more medical devices on the first list of medical devices is the identified medical device.

9. The system of claim 8, wherein, after the interface module displays the first list, the interface module receives an additional search heuristic, and wherein the device discovery manager applies the additional search heuristic to the first list, and the interface module displays a second list of one or more medical devices in the subset that results from applying the additional search heuristic to the first list.

10. The system of claim 1, further comprising a telemetry device that is capable of communicating with the programming system and one or more of the set of discovered medical devices,
wherein the programming system communicates with the telemetry device, and wherein the device discovery manager queries the telemetry device for information regarding the medical devices in the set and uses the information regarding the medical devices in the set as the one or more of the search heuristics.

11. The system of claim 10, wherein the programming system communicates with one or more medical devices in the subset via the telemetry device.

12. The system of claim 10, wherein the telemetry device comprises a wireless communications module to facilitate wireless communication with the programming system.

13. The system of claim 10, wherein the telemetry device comprises a wireless communications module to facilitate wireless communication with one or more of the set of discovered medical devices.

14. The system of claim 10, wherein one of the set of discovered medical devices communicates with the telemetry device when a patient associated with the one of the set of discovered medical devices indicates consent to communication between the one of the set of discovered medical devices and the telemetry device.

15. The system of claim 14, wherein the telemetry device comprises:
a sensor that detects whether the telemetry device is within close proximity to the patient, and
a module that outputs signals that enable the one of the set of discovered medical devices to communicate with the telemetry device when the telemetry device is within close proximity to the patient.

16. The system of claim 14, wherein the telemetry device comprises an interface by which the patient provides input that indicates the consent of the patient.

17. The system of claim 10, wherein the telemetry device is bonded to the one of the set of discovered medical devices.

18. The system of claim 10, wherein the telemetry device comprises a patient programming device.

19. The system of claim 1, wherein the set of discovered medical devices comprise a set of implantable medical devices.

20. The system of claim 1, wherein the user interacts with the identified medical device by at least one of programming the identified medical device and retrieving data from the identified medical device.

21. The system of claim 1, wherein the programming system comprises a first programming system, the system further comprising:
a second programming system; and
a plurality of telemetry devices that are each configured to communicate with the first programming system and the second programming system,
wherein each medical device in the set of medical devices is configured to communicate with the first programming system and the second programming system.

22. The system of claim 1, further comprising the set of medical devices.

* * * * *